United States Patent
Fukumoto et al.

(10) Patent No.: US 10,858,393 B2
(45) Date of Patent: Dec. 8, 2020

(54) CRYSTAL OF REDUCED GLUTATHIONE AND METHOD FOR PRODUCING SAME

(71) Applicant: KYOWA HAKKO BIO CO., LTD., Tokyo (JP)

(72) Inventors: Kazunari Fukumoto, Tokyo (JP); Maya Iguchi, Tokyo (JP); Hiroshi Nagano, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 42 days.

(21) Appl. No.: 16/083,487

(22) PCT Filed: Mar. 10, 2017

(86) PCT No.: PCT/JP2017/009660
§ 371 (c)(1),
(2) Date: Sep. 7, 2018

(87) PCT Pub. No.: WO2017/159555
PCT Pub. Date: Sep. 21, 2017

(65) Prior Publication Data
US 2019/0071466 A1  Mar. 7, 2019

(30) Foreign Application Priority Data
Mar. 17, 2016 (JP) ................................ 2016-053844

(51) Int. Cl.
| | | |
|---|---|---|
| *C07K 5/02* | (2006.01) |
| *C30B 29/54* | (2006.01) |
| *C30B 7/14* | (2006.01) |
| *C30B 33/00* | (2006.01) |
| *C30B 7/08* | (2006.01) |
| *C30B 7/10* | (2006.01) |
| *C30B 29/58* | (2006.01) |
| *C07K 5/062* | (2006.01) |
| *A61K 38/06* | (2006.01) |

(52) U.S. Cl.
CPC ............ *C07K 5/0215* (2013.01); *C30B 7/08* (2013.01); *C30B 7/10* (2013.01); *C30B 7/14* (2013.01); *C30B 29/54* (2013.01); *C30B 29/58* (2013.01); *C30B 33/00* (2013.01); *A61K 38/06* (2013.01); *C07K 5/0606* (2013.01)

(58) Field of Classification Search
None
See application file for complete search history.

(56) References Cited

U.S. PATENT DOCUMENTS

| | | | |
|---|---|---|---|
| 8,188,308 B2 * | 5/2012 | Shimose | C07K 5/0215 562/29 |
| 9,028,669 B2 * | 5/2015 | Fukumoto | C07K 5/0215 205/435 |
| 2018/0170959 A1 | 6/2018 | Iguchi et al. | |

FOREIGN PATENT DOCUMENTS

| | | |
|---|---|---|
| JP | S44-000239 B | 1/1969 |
| JP | S45-004755 B | 2/1970 |
| JP | S45-027797 B | 9/1970 |
| JP | S46-002838 B | 1/1971 |
| JP | S52-131528 A | 11/1977 |
| JP | S60-258199 A | 12/1985 |
| JP | S61-027999 A | 2/1986 |
| JP | S61-282397 A | 12/1986 |
| JP | S62-283994 A | 12/1987 |
| WO | WO 2016/195070 A1 | 12/2016 |

OTHER PUBLICATIONS

Product information for Strong Cationic Resins downloaded from www.itochu-ca.com/docs/product/00500-013.pdf (Year: 2020).*
Dominici et al., "γ-Glutamyltransferase-dependent prooxidant reactions: A factor in multiple processes," *BioFactors*, 17: 187-198 (2003).
Li et al., "Glutathione: a review on biotechnological production," *Appl. Microbiol. Biotechnol.*, 66: 233-242 (2004).
Paolicchi et al., "γ-Glutamyl Transpeptidase-Dependent Iron Reduction and LDL Oxidation—A Potential Mechanism in Atherosclerosis," *Journal of Investigative Medicine*, 47(3): 151-160 (1999).
Japanese Patent Office, International Search Report in International Patent Application No. PCT/JP2017/009660 (dated Jun. 6, 2017).
European Patent Office, Extended European Search Report in European Patent Application No. 17766555.1 (dated Sep. 17, 2019).
Japanese Patent Office, International Preliminary Report on Patentability in International Patent Application No. PCT/JP2017/009660 (dated Sep. 18, 2018).
Yamasaki et al., "Analytical studies of polymorphism of glutathione," *Japan Analyst*, 18(7): 874-878 (1969).

* cited by examiner

*Primary Examiner* — Christina Bradley
(74) *Attorney, Agent, or Firm* — Leydig, Voit & Mayer, Ltd.

(57) ABSTRACT

According to the present invention, a crystal of reduced glutathione having a reduced content of impurities, particularly L-cysteinyl-L-glycine and a method for producing the same are provided. The present invention relates to a crystal of reduced glutathione, wherein, in a high-performance liquid chromatography (HPLC) analysis, the peak area of L-cysteinyl-L-glycine is 0.02 or less with respect to the peak area of reduced glutathione which is taken as 100.

12 Claims, 1 Drawing Sheet

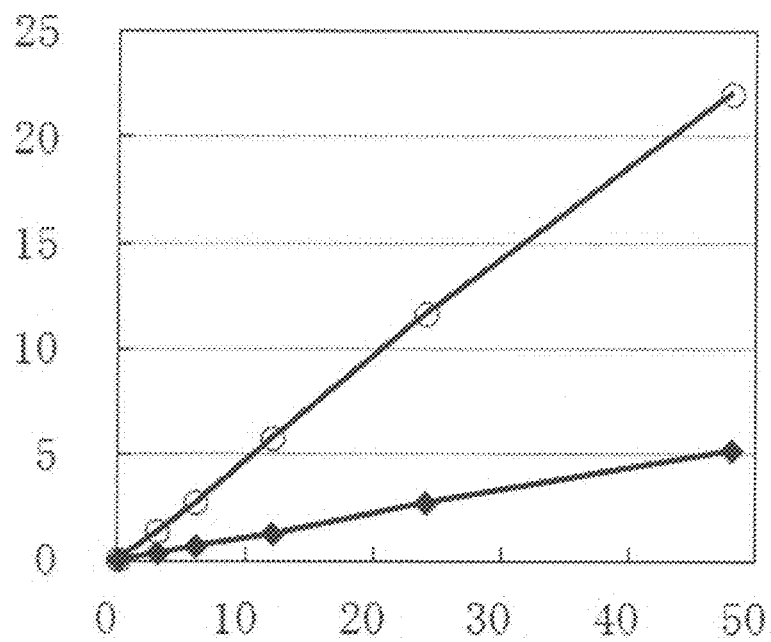

CRYSTAL OF REDUCED GLUTATHIONE AND METHOD FOR PRODUCING SAME

CROSS-REFERENCE TO RELATED APPLICATIONS

This patent application is the U.S. national phase of International Patent Application No. PCT/JP2017/009660, filed Mar. 10, 2017, which claims the benefit of Japanese Patent Application No. 2016-053844, filed on Mar. 17, 2016, which are incorporated by reference in their entireties herein.

TECHNICAL FIELD

The present invention relates to a crystal of reduced glutathione having a reduced content of impurities, particularly L-cysteinyl-L-glycine and a method for producing the same.

BACKGROUND ART

Glutathione (γ-L-glutamyl-L-cysteinyl-L-glycine) is a reducing compound widely existing in organisms and is known to have a detoxification effect in the liver. Therefore, glutathione has been widely used as a product such as a pharmaceutical product, a health food, and a cosmetic product, or a raw material or an intermediate thereof.

As a method for producing glutathione, a fermentation method using a microorganism such as yeast, an enzymatic method (Non-Patent Document 1), etc. are known, however, there is a problem that an analog impurity having a similar structure is produced as a by-product.

As a method for purifying glutathione, a method in which copper suboxide and a copper salt are formed and a method in which glutathione is adsorbed onto a strongly acidic ion exchange resin and glutathione is eluted with an acid or a base (Patent Documents 1 to 3), and a method in which glutathione is passed through a weakly basic anion exchange resin (Patent Document 4) are known, however, glutathione is easily reacted or decomposed by heating, oxidation, pH change, or the like to produce a lot of impurities.

Among these impurities, particularly, L-cysteinyl-L-glycine is known to generate free radicals causing various diseases (Non-Patent Documents 2 and 3). Further, in the Guideline for Impurities in Pharmaceutical Drug Substances issued by Ministry of Health, Labour and Welfare, each impurity contained in glutathione needs to be reduced to 0.05% or less at minimum depending on the maximum daily dose of a drug substance.

In this manner, in glutathione as a raw material of a pharmaceutical product or a food, reduction in impurities is strongly demanded from the viewpoint of safety. As a method for purifying glutathione, Patent Document 5 discloses a method in which a specific impurity such as cysteine or γ-glutamylcysteine is removed. However, there has been no report so far on a method for removing L-cysteinyl-L-glycine.

RELATED ART

Patent Documents

Patent Document 1: JP-B-44-239
Patent Document 2: JP-B-45-4755
Patent Document 3: JP-B-46-2838
Patent Document 4: JP-B-45-27797
Patent Document 5: JP-A-61-282397

Non-Patent Documents

Non-Patent Document 1: Appl. Microbiol. Biotechnol., 66, 233 (2004)
Non-Patent Document 2: J. Investig. Med., Vol. 47, No. 3, 151-160 (1999)
Non-Patent Document 3: BioFactors., 17, 187-198 (2003)

DISCLOSURE OF INVENTION

Problems to be Solved by the Invention

As described above, it was difficult to reduce L-cysteinyl-L-glycine by the conventional method. In view of this, an object of the present invention is to provide a crystal of reduced glutathione having a reduced content of impurities, particularly L-cysteinyl-L-glycine and a method for producing the same.

Means for Solving the Problems

The present invention relates to the following (1) to (7).
(1) A crystal of reduced glutathione, wherein, in a high-performance liquid chromatography (HPLC) analysis, the peak area of L-cysteinyl-L-glycine is 0.02 or less with respect to the peak area of reduced glutathione which is taken as 100.
(2) The crystal of reduced glutathione described in (1), wherein in an HPLC analysis, the peak area of oxidized glutathione is 0.7 or less with respect to the peak area of reduced glutathione which is taken as 100.
(3) The crystal of reduced glutathione described in (1) or (2), wherein in an HPLC analysis, the total area of the other peaks is 1.0 or less with respect to the peak area of reduced glutathione which is taken as 100.
(4) The crystal of reduced glutathione described in any one of (1) to (3), wherein in an HPLC analysis, the area of each of the other peaks excluding the peak of oxidized glutathione is 0.08 or less with respect to the peak area of reduced glutathione which is taken as 100.
(5) A method for producing a crystal of reduced glutathione in which in an HPLC analysis, the peak area of L-cysteinyl-L-glycine is 0.02 or less with respect to the peak area of reduced glutathione which is taken as 100, wherein the method comprising passing an aqueous solution containing reduced glutathione through a cation exchange resin with a high crosslinking degree, recovering the aqueous solution, precipitating a crystal of reduced glutathione in the aqueous solution, and collecting the crystal of reduced glutathione from the aqueous solution.
(6) The production method described in (5), wherein the cation exchange resin with a high crosslinking degree is a cation exchange resin having a crosslinking degree of 12% or more.
(7) The production method described in (5) or (6), wherein the cation exchange resin with a high crosslinking degree is a cation exchange resin having a sulfone group as a cation exchange group.

Effects of the Invention

According to the present invention, a crystal of reduced glutathione having a reduced content of impurities, particularly L-cysteinyl-L-glycine and a method for producing the same are provided.

BRIEF DESCRIPTION OF THE DRAWINGS

FIG. 1 illustrates an increasing profile for L-cysteinyl-L-glycine in an aqueous solution containing reduced glutathione. The vertical axis represents the peak area of L-cysteinyl-L-glycine with respect to the peak area of reduced glutathione which is taken as 100 in an HPLC analysis of the aqueous solution. The vertical axis represents the time (h). In FIG. 1, the white circles indicate the results at 40° C., and the black lozenges indicate the results at 25° C.

EMBODIMENTS FOR CARRYING OUT THE INVENTION

1. Crystal of the Present Invention

In the crystal of reduced glutathione of the present invention (hereinafter also referred to as "the crystal of the present invention"), in an HPLC analysis, the peak area of L-cysteinyl-L-glycine is 0.02 or less, preferably 0.015 or less, more preferably 0.01 or less, most preferably 0.006 or less with respect to the peak area of reduced glutathione which is taken as 100.

In the crystal of the present invention, in an HPLC analysis, the peak area of oxidized glutathione is preferably 0.7 or less, more preferably 0.6 or less, further more preferably 0.5 or less with respect to the peak area of reduced glutathione which is taken as 100.

In the crystal of the present invention, in an HPLC analysis, the total area of the other peaks is preferably 1.0 or less, more preferably 0.9 or less, further more preferably 0.8 or less, most preferably 0.7 or less with respect to the peak area of reduced glutathione which is taken as 100.

In the crystal of the present invention, in an HPLC analysis, the area of each of the other peaks excluding the peak of oxidized glutathione is preferably 0.08 or less, more preferably 0.06 or less, further more preferably 0.04 or less, most preferably 0.02 or less with respect to the peak area of reduced glutathione which is taken as 100.

The HPLC analysis means that a compound to be analyzed is dissolved in a solvent and subjected to an analysis by HPLC. The analysis conditions, etc. for the HPLC analysis are not particularly limited as long as it is an analysis method capable of simultaneously detecting reduced glutathione, oxidized glutathione, and L-cysteinyl-L-glycine, and preferably, an HPLC analysis method in which an absorbance at 210 nm is detected and measured can be exemplified, and more preferably, an HPLC analysis method described in the following HPLC Analysis Example can be exemplified.

[HPLC Analysis Example]

In order to prevent an increase in purities during an HPLC analysis, the time between when a sample is dissolved and when the analysis is performed by HPLC is determined to be within 10 minutes. Further, an HPLC sample rack is cooled to 10° C. or lower. The determination limit and the detection limit under the conditions are 0.001 with respect to the peak area of reduced glutathione which is taken as 100.

Used device: a system controller (CBM-20A), a detector (SPD-20A), a pump (LC-20AD), an autosampler (SIL-20ACHT), a column oven (CTO-20AC), and a degasser (DGU-20A) (all manufactured by Shimadzu Corporation)

Detector: an ultraviolet absorption spectrophotometer (measurement wavelength: 210 nm)

Column: Inertsil ODS-3, particle size 3 μm, 3.0×150 mm (GL Sciences, Inc.)

Mobile phase: a 3 W/V % methanol solution (adjusted to pH 3.0 with phosphoric acid) containing 0.20 W/V % sodium 1-heptanesulfonate and 0.66 W/V % potassium dihydrogen phosphate The mobile phase is prepared by dissolving 6.8 g of potassium dihydrogen phosphate and 2.02 g of sodium 1-heptanesulfonate in 1000 mL of PFW, adjusting the pH to 3.0 by adding phosphoric acid thereto, and then, adding 30 mL of methanol to 970 mL of this solution.

Column temperature: 35° C.

Flow rate: 0.4 to 0.7 mL/min (adjusted so that the retention time of reduced glutathione is about 5 minutes)

Sample injection volume: 30 μL

Sample preparation method: About 0.05 g of a sample is weighed and dissolved in 100 mL of the mobile phase, and the resulting solution is used as the sample.

The peak area refers to an area of a portion surrounded by a baseline and a peak line when performing an HPLC analysis, and can be determined for each compound detected by the HPLC analysis.

As the crystal of the present invention, a crystal of reduced glutathione in which in an HPLC analysis, with respect to the peak area of reduced glutathione which is taken as 100, the peak area of L-cysteinyl-L-glycine is 0.02 or less, and in addition thereto, the peak area of oxidized glutathione is preferably 0.7 or less, more preferably 0.6 or less, further more preferably 0.5 or less is exemplified.

Further, as the crystal of the present invention, a crystal of reduced glutathione in which in an HPLC analysis, with respect to the peak area of reduced glutathione which is taken as 100, the peak area of L-cysteinyl-L-glycine is 0.02 or less, and in addition thereto, the total area of the other peaks is preferably 1.0 or less, more preferably 0.9 or less, further more preferably 0.8 or less, most preferably 0.7 or less is exemplified.

Further, as the crystal of the present invention, a crystal of reduced glutathione in which in an HPLC analysis, with respect to the peak area of reduced glutathione which is taken as 100, the peak area of L-cysteinyl-L-glycine is 0.02 or less, and in addition thereto, the area of each of the other peaks excluding the peak of oxidized glutathione is preferably 0.08 or less, more preferably 0.06 or less, further more preferably 0.04 or less, most preferably 0.02 or less is exemplified.

As the crystal of the present invention, specifically, for example, a crystal of reduced glutathione in which the retention time and the peak area of each compound in an HPLC analysis are represented by the numerical values shown in Table 3 (Examples 3 and 4) can be exemplified.

2. Method for Producing Crystal of the Present Invention

The method for producing a crystal of the present invention is a method comprising passing an aqueous solution containing reduced glutathione through a cation exchange resin with a high crosslinking degree, recovering the aqueous solution, precipitating a crystal of reduced glutathione in the aqueous solution, and collecting the crystal of reduced glutathione from the aqueous solution.

The aqueous solution containing reduced glutathione to be used in the production method of the present invention may be a solution produced by any production method of a fermentation method, an enzymatic method, an extraction method from a natural product, a chemical synthesis method, and the like, however, for example, a solution obtained by removing insoluble substances from a culture containing reduced glutathione obtained by culturing a microorganism having an ability to produce glutathione (WO 2008/126784), an aqueous solution containing reduced glutathione obtained by an enzymatic method [Appl. Microbiol. Biotechnol., 66, 233 (2004), JP-A-60-105499, etc.], or the like can be exemplified.

Further, the aqueous solution containing reduced glutathione may be an aqueous solution containing reduced glutathione obtained by reducing oxidized glutathione hexahydrate. The oxidized glutathione hexahydrate can be obtained according to the method described in WO 2011/132724.

The aqueous solution containing reduced glutathione can be obtained by dissolving oxidized glutathione hexahydrate in an aqueous solution, and subjecting the oxidized glutathione-containing aqueous solution to electrolytic reduction according to the method described in WO 2012/137824, WO 2010/140625, or WO 2014/133129. By obtaining oxidized glutathione as a crystal of oxidized glutathione hexahydrate, impurities can be more efficiently removed (WO 2011/132724).

The term "impurities" as used herein refers to all compounds other than reduced glutathione contained in the crystal of reduced glutathione.

As the method for passing an aqueous solution containing reduced glutathione through a cation exchange resin with a high crosslinking degree, for example, a method for passing an aqueous solution containing reduced glutathione through a column packed with an ion exchange resin with a high crosslinking degree can be exemplified.

In the case where a solid material which becomes an obstacle when passing through the cation exchange resin with a high crosslinking degree is contained in the aqueous solution containing reduced glutathione, the solid material can be removed in advance using centrifugation, filtration, a ceramic filter, or the like.

Further, in the case where a water-soluble impurity which becomes an obstacle when passing through the cation exchange resin with a high crosslinking degree is contained in the aqueous solution containing reduced glutathione, the impurity can be removed by passing the aqueous solution containing reduced glutathione through a column packed with an ion exchange resin or the like.

Further, in the case where a hydrophobic impurity which becomes an obstacle when passing through the cation exchange resin with a high crosslinking degree is contained in the aqueous solution containing reduced glutathione, the impurity can be removed by passing the aqueous solution containing reduced glutathione through a column packed with a synthetic adsorption resin, active carbon, or the like.

As the concentration of reduced glutathione in the aqueous solution containing reduced glutathione, generally 25 g/L or more, preferably 50 g/L or more, more preferably 100 g/L or more can be exemplified.

The aqueous solution containing reduced glutathione having such a concentration can be obtained by concentrating the aqueous solution by a general concentration method such as a heating concentration method or a reduced pressure concentration method.

The pH of the aqueous solution containing reduced glutathione is generally 2.0 to 10.0, preferably 2.0 to 7.0, and according to need, the pH of the aqueous solution can be adjusted within the above range using an inorganic or organic acid such as hydrochloric acid, sulfuric acid, acetic acid, or malic acid, an alkaline solution of sodium hydroxide or the like, urea, calcium carbonate, ammonia, or the like.

The saturation solubility of glutathione in water is 83 g/L at 10° C. and 130 g/L at 25° C., but is known to increase when increasing the pH (WO 2011/137824). Therefore, by adding a base to the aqueous solution containing reduced glutathione to increase the pH, the concentration of glutathione can be further increased.

As the crosslinking degree of the cation exchange resin with a high crosslinking degree to be used in the production method of the present invention, for example, generally 12% or more, preferably 14% or more, more preferably 15% or more, most preferably 16% or more can be exemplified. The crosslinking degree refers to the weight ratio of a crosslinking agent relative to the entire raw materials constituting an ion exchange resin in the resin.

As the crosslinking agent of the cation exchange resin with a high crosslinking degree, for example, divinylbenzene can be exemplified. As the cation exchange group of the cation exchange resin with a high crosslinking degree, for example, a sulfone group can be exemplified.

The ion type of the cation exchange resin with a high crosslinking degree is not particularly limited as long as it has an ability to adsorb L-cysteinyl-L-glycine, however, for example, a hydrogen ion type can be exemplified. As the particle diameter of the cation exchange resin with a high crosslinking degree, for example, generally 300 to 900 μm, preferably 400 to 800 μm, most preferably 500 to 700 μm can be exemplified.

As the cation exchange resin with a high crosslinking degree to be used in the production method of the present invention, specifically, for example, cation exchange resins having a high crosslinking degree selected from the group consisting of UBK12, UBKN1U, UBK16, SK110, SK112, PK220, and PK228 (all manufactured by Mitsubishi Chemical Corporation), C100×16MBH, C100×12, and C100×10 (all manufactured by Puroite, Inc.), Amberlite (trademark) 200CT and Amberlite (trademark) 252 (both manufactured by Rohm and Haas Company), preferably, UBK12, UBKN1U, and UBK16 (all manufactured by Mitsubishi Chemical Corporation) can be exemplified.

In the production method of the present invention, the amount of the cation exchange resin with a high crosslinking degree can be easily set by a person skilled in the art according to the pH and amount of the aqueous solution containing reduced glutathione to be passed through the cation exchange resin with a high crosslinking degree, and for example, generally 0.1 to 5 times the amount of the aqueous solution.

As the temperature when the aqueous solution containing reduced glutathione is passed through the cation exchange resin with a high crosslinking degree, generally 5 to 40° C., preferably 10 to 35° C., most preferably 15 to 30° C. can be exemplified.

The velocity when the aqueous solution containing reduced glutathione is passed through the cation exchange resin with a high crosslinking degree is not particularly limited as long as the ability to remove L-cysteinyl-L-glycine is not deteriorated, and a liquid hourly space velocity (SV) of generally 0.1 to 10.0, preferably 0.2 to 9.0, more preferably 0.3 to 8.0, most preferably 0.5 to 5.0 can be exemplified. The liquid hourly space velocity (SV) refers to a value obtained by dividing the liquid feeding amount (L/h) by the resin packing amount (L).

An aqueous solution containing reduced glutathione obtained by passing through the cation exchange resin with a high crosslinking degree is desalted by passing through an ion exchange resin, and the desalted aqueous solution containing reduced glutathione can be directly used for precipitation of a crystal of reduced glutathione.

As the ion exchange resin to be used in desalting, for example, a weakly basic ion exchange resin represented by WA-30 and WA-21 [both Diaion (trademark), manufactured by Mitsubishi Chemical Corporation] can be exemplified.

As the method for precipitating a crystal of reduced glutathione may be any method as long as it is a method capable of precipitating reduced glutathione as a crystal, and for example, a method in which a seed crystal of reduced glutathione and a solvent are added to an aqueous solution containing reduced glutathione described in Japanese Patent No. 5243963 can be exemplified.

Further, a method in which an α-type crystal of glutathione is selectively crystallized in an aqueous solution containing reduced glutathione (Japanese Patent No. 5243963), and to the aqueous solution containing the α-type crystal of glutathione, an aqueous solution in which the concentration of glutathione is increased to not less than the saturation solubility is added continuously or dividedly, whereby a crystal of reduced glutathione is precipitated may be used.

The method for collecting the crystal of reduced glutathione is not particularly limited, and collection by filtration, pressure filtration, suction filtration, centrifugation, and the like can be exemplified. Further, in order to reduce the adhesion of the mother liquor to the crystal so as to improve the quality of the crystal, after collecting the crystal, the crystal can be washed as appropriate.

A solution to be used for washing is not particularly limited, and water, methanol, ethanol, acetone, n-propanol, isopropyl alcohol, and one type of solution selected therefrom, or a solution obtained by mixing a plurality of types selected therefrom at an arbitrary ratio can be used.

By the above-mentioned method, the crystal of reduced glutathione of the present invention can be obtained, and in the case where the obtained crystal is a wet crystal, a crystal which is easy to handle can be obtained by drying. The drying condition may be any condition as long as it is a method capable of maintaining the form of the crystal of reduced glutathione, and for example, reduced pressure drying, vacuum drying, fluidized bed drying, ventilation drying, and the like are exemplified.

The drying temperature may be any temperature as long as adhesive water or a solution can be removed, and the crystal of reduced glutathione is not decomposed, however, generally, 70° C. or lower, preferably 60° C. or lower, more preferably 50° C. or lower can be exemplified.

EXAMPLES

Hereinafter, Examples will be shown, however, the present invention is not limited to the following Examples.

Reference Example

An α-type crystal of reduced glutathione (manufactured by Kojin Co., Ltd.) was dissolved in water, and thereafter, the solution was adjusted to 100 g/L and hermetically sealed and placed in a thermostat bath at 25° C. or 40° C. while stirring. These reduced glutathione aqueous solutions were sampled over time and subjected to an HPLC analysis. From the results shown in FIG. 1, it was found that reduced glutathione is decomposed over time in a temperature-dependent manner to produce L-cysteinyl-L-glycine.

Comparative Example

An aqueous solution containing reduced glutathione at a concentration of 183 g/L was prepared according to the method described in Example 1 of Japanese Patent No. 5243963. The aqueous solution was directly concentrated to 539 g/L by heating under reduced pressure. While maintaining the obtained concentrated solution at 25° C., an α-type crystal of reduced glutathione (manufactured by Kojin Co., Ltd.) was added to the concentrated solution as a seed crystal. After the seed crystal was added, stirring was performed at 25° C. for 10 hours, whereby an aqueous solution in which the α-type crystal of reduced glutathione started to form was obtained.

After the obtained aqueous solution was cooled to 10° C., 0.3 times equivalent of ethanol was added to the aqueous solution, whereby the α-type crystal of reduced glutathione was crystallized. The obtained slurry was centrifuged to remove the aqueous solution layer, and thereafter, the crystal was washed with 60 v/v % ethanol, and then dried under reduced pressure at 40° C., whereby the α-type crystal of reduced glutathione was obtained.

Example 1

After a crystal of reduced glutathione obtained by the method described in Japanese Patent No. 5243963 was dissolved in water, the resulting solution was heated at 60° C. for 1 hour, whereby the content of L-cysteinyl-L-glycine was increased. Thereafter, aqueous solutions containing reduced glutathione at a concentration of 100 g/L, 50 g/L, or 25 g/L were prepared.

These aqueous solutions in an amount of 670 mL, 1340 mL, and 2680 mL, respectively, was passed through a glass column having a diameter of 2 cm packed with 100 mL of UBK16 (manufactured by Mitsubishi Chemical Corporation) regenerated into a hydrogen ion type at a liquid hourly space velocity (SV) of 1.0 (100 mL/h) as the flow rate under room temperature. After the reduced glutathione aqueous solution was passed through the column, the UBK16 was washed with water until the sugar content (Brix) was decreased to 1% or less, and a reduced glutathione fraction was recovered. The results of the yield of reduced glutathione, the removal ratio of L-cysteinyl-L-glycine, and the ratio of increase in the liquid amount are shown in Table 1.

TABLE 1

| Concentration of reduced glutathione before passing through resin [g/L] | Yield of reduced glutathione [%] | Removal ratio of L-cysteinyl-L-glycine [%] | Ratio of increase in liquid amount [%] |
|---|---|---|---|
| 100 | 94 | 87 | 107 |
| 50 | 91 | 94 | 100 |
| 25 | 83 | 93 | 93 |

As shown in Table 1, it was found that by using a cation exchange resin with a high crosslinking degree, the increase in the liquid amount after passing the reduced glutathione-containing aqueous solution through the column is suppressed at any concentration of reduced glutathione in the aqueous solution containing reduced glutathione, and also L-cysteinyl-L-glycine can be selectively adsorbed and removed without largely decreasing the yield of reduced glutathione.

Example 2

A crystal of reduced glutathione obtained by the method described in Japanese Patent No. 5243963 was dissolved in water, and the resulting solution was heated at 60° C. for 1 hour, thereby increasing the content of L-cysteinyl-L-glycine. Thereafter, an aqueous solution containing reduced glutathione at a concentration of 100 g/L was prepared.

Glass columns having a diameter of 2 cm packed with 100 mL of UBKN1U (crosslinking degree: 14%), UBK12 (crosslinking degree: 12%), UBK08 (crosslinking degree: 8%), or UBK06 (crosslinking degree: 6%) (all manufactured by Mitsubishi Chemical Corporation), each of which was regenerated into a hydrogen ion type, were prepared, and the aqueous solution was passed through UBKN1U (amount of aqueous solution: 643 mL), UBK12 (amount of aqueous solution: 616 mL), UBK08 (amount of aqueous solution: 536 mL), or UBK06 (amount of aqueous solution: 482 mL) at an SV of 1.0 (100 mL/h) as the flow rate under room temperature. The amount of the aqueous solution containing reduced glutathione to be passed through the column was adjusted according to the total exchange capacity of each resin.

After passing the aqueous solution containing reduced glutathione through the column, a reduced glutathione fraction was recovered by washing each resin with water until the sugar content (Brix) decreased below 1%. The results of the yield of reduced glutathione, the removal ratio of L-cysteinyl-L-glycine, and the ratio of increase in the liquid amount are shown in Table 2.

TABLE 2

| Resin | Crosslinking degree [%] | Yield of reduced glutathione [%] | Removal ratio of L-cysteinyl-L-glycine [%] | Ratio of increase in liquid amount [%] |
|---|---|---|---|---|
| UBK06 | 6 | 32 | 86 | 245 |
| UBK08 | 8 | 39 | 83 | 187 |
| UBK12 | 12 | 70 | 81 | 102 |
| UBKN1U | 14 | 79 | 84 | 104 |
| UBK16 | 16 | 94 | 84 | 107 |

As shown in Table 2, it was found that by using a cation exchange resin with a high crosslinking degree, which has a crosslinking degree of 12% or more, the increase in the liquid amount after passing the aqueous solution containing reduced glutathione through the column is suppressed, and also L-cysteinyl-L-glycine can be selectively adsorbed and removed without largely decreasing the yield of reduced glutathione.

Example 3

Production of Crystal of the Present Invention (1)

Oxidized glutathione obtained by the method described in WO 2011/132724 was reduced by the method described in WO 2012/137824, whereby an aqueous solution containing reduced glutathione at a concentration of 164 g/L was obtained. While maintaining the obtained reduced glutathione-containing aqueous solution at 25° C., the aqueous solution was passed through a column packed with UBK16 (manufactured by Mitsubishi Chemical Corporation) regenerated into a hydrogen ion type at a liquid hourly space velocity SV of 2.5, whereby a fraction containing reduced glutathione was obtained.

This fraction was concentrated to 530 g/L by heating under reduced pressure. While maintaining the obtained concentrated solution at 25° C., an α-type crystal of reduced glutathione (manufactured by Kojin Co., Ltd.) was added thereto as a seed crystal. After the seed crystal was added, stirring was performed at 25° C. for 17 hours, whereby an aqueous solution in which the α-type crystal of reduced glutathione started to form was obtained. After the obtained aqueous solution was cooled to 10° C., 0.3 times equivalent of ethanol was added to the aqueous solution, whereby the α-type crystal of reduced glutathione was crystallized.

The obtained slurry was centrifuged to remove the aqueous solution layer, and thereafter, the crystal was washed with 30 v/v % ethanol, and then dried by ventilation at 40° C., whereby the α-type crystal of reduced glutathione which is the crystal of the present invention was obtained.

Example 4

Production of Crystal of the Present Invention (2)

Oxidized glutathione obtained by the method described in WO 2011/132724 was reduced by the method described in WO 2012/137824, whereby an aqueous solution containing reduced glutathione at a concentration of 173 g/L was obtained.

While maintaining the obtained reduced glutathione-containing aqueous solution at 25° C., the aqueous solution was passed through a column packed with UBK16 (manufactured by Mitsubishi Chemical Corporation) regenerated into a hydrogen ion type at a liquid hourly space velocity SV of 2.5, whereby a fraction containing reduced glutathione was obtained. This fraction was concentrated to 426 g/L by heating under reduced pressure. While maintaining the obtained concentrated solution at 25° C., an α-type crystal of reduced glutathione (manufactured by Kojin Co., Ltd.) was added thereto as a seed crystal. After the seed crystal was added, stirring was performed at 25° C. for 19 hours, whereby an aqueous solution in which the α-type crystal of reduced glutathione started to form was obtained.

After the obtained aqueous solution was cooled to 10° C., 0.3 times equivalent of ethanol was added to the aqueous solution, whereby the α-type crystal of reduced glutathione was precipitated. The obtained slurry was centrifuged to remove the aqueous solution layer, and thereafter, the crystal was washed with 30 v/v % ethanol, and then dried by ventilation at 40° C., whereby the α-type crystal of reduced glutathione which is the crystal of the present invention was obtained.

Commercially available crystals of reduced glutathione (commercially available products A and B), the crystal of reduced glutathione obtained in Comparative Example, and the crystals of the present invention obtained in Examples 3 and 4 were analyzed by HPLC, and impurities contained in the crystals were measured. The results of the HPLC analysis are shown in Table 3. In Table 3, each peak area is shown when the peak area of reduced glutathione was taken as 100.

Further, in Table 3, "N.D" indicates that the result is equal to or less than the detection limit, "glutathione" indicates reduced glutathione, "γGC-Ala" indicates γ-L-glutamyl-L-cysteinyl-L-alanine, "CysGly" indicates L-cysteinyl-L-glycine, and "GSSG" indicates oxidized glutathione.

TABLE 3

| Compound | Retention time [min] | Commercially available product A | Commercially available product B | Comparative Example | Example 3 | Example 4 |
|---|---|---|---|---|---|---|
| | 1.2 | 0.046 | 0.010 | 0.005 | 0.010 | 0.007 |
| | 1.6 | 0.002 | 0.002 | 0.001 | 0.000 | 0.001 |
| | 2.1 | 0.019 | 0.011 | 0.010 | 0.030 | 0.007 |
| | 2.2 | 0.011 | 0.009 | 0.008 | 0.008 | 0.006 |

TABLE 3-continued

| Compound | Retention time [min] | Commercially available product A | Commercially available product B | Comparative Example | Example 3 | Example 4 |
|---|---|---|---|---|---|---|
| | 2.3 | N.D | 0.004 | N.D | N.D | N.D |
| | 2.5 | N.D | 0.004 | N.D | N.D | N.D |
| | 2.7 | 0.039 | N.D | 0.045 | N.D | N.D |
| | 2.9 | N.D | 0.003 | N.D | 0.002 | 0.003 |
| | 3.1 | N.D | N.D | N.D | 0.002 | 0.003 |
| | 3.3 | 0.027 | 0.015 | N.D | N.D | N.D |
| | 3.4 | N.D | N.D | 0.051 | N.D | N.D |
| | 4.0 | 0.030 | 0.015 | 0.012 | 0.008 | 0.007 |
| | 4.5 | 0.072 | 0.118 | N.D | 0.013 | 0.015 |
| glutathione | 5.2 | 100 | 100 | 100 | 100 | 100 |
| | 6.0 | N.D | N.D | 0.049 | N.D | N.D |
| | 6.3 | 0.001 | N.D | N.D | 0.002 | N.D |
| | 6.6 | 0.004 | N.D | 0.056 | N.D | N.D |
| | 6.9 | 0.001 | N.D | N.D | N.D | N.D |
| | 7.4 | 0.002 | 0.009 | N.D | N.D | N.D |
| | 7.6 | 0.003 | 0.008 | N.D | N.D | N.D |
| γ-GC-Ala | 8.1 | 0.052 | 0.125 | 0.047 | 0.001 | 0.001 |
| | 8.7 | N.D | N.D | N.D | 0.004 | 0.003 |
| | 9.2 | 0.038 | 0.055 | 0.018 | 0.015 | 0.006 |
| | 10.1 | 0.017 | 0.017 | 0.002 | N.D | N.D |
| | 10.3 | N.D | N.D | N.D | 0.012 | 0.012 |
| | 11.0 | N.D | N.D | 0.002 | N.D | N.D |
| | 11.2 | 0.005 | 0.005 | N.D | N.D | N.D |
| | 11.7 | N.D | N.D | 0.002 | N.D | N.D |
| CysGly | 12.7 | 0.045 | 0.025 | 0.030 | 0.004 | 0.001 |
| | 13.3 | 0.032 | 0.015 | 0.007 | 0.009 | 0.007 |
| | 14.2 | 0.090 | 0.067 | N.D | 0.002 | 0.002 |
| | 15.4 | 0.018 | 0.005 | N.D | N.D | N.D |
| GSSG | 17.5 | 0.543 | 0.463 | 0.733 | 0.435 | 0.462 |
| | 19.1 | 0.019 | 0.024 | 0.004 | 0.012 | 0.010 |
| | 19.4 | N.D | N.D | N.D | 0.005 | N.D |
| | 20.5 | 0.003 | N.D | N.D | N.D | N.D |
| | 21.9 | 0.013 | 0.009 | N.D | N.D | N.D |
| | 22.9 | N.D | N.D | 0.005 | N.D | N.D |
| | 24.9 | 0.005 | 0.003 | 0.010 | 0.002 | N.D |
| | 27.4 | 0.008 | N.D | N.D | N.D | N.D |
| | 28.7 | 0.030 | N.D | N.D | N.D | N.D |
| | 29.9 | N.D | 0.007 | N.D | N.D | N.D |
| | 34.0 | N.D | 0.009 | N.D | N.D | N.D |
| | 34.4 | 0.009 | N.D | 0.032 | 0.007 | N.D |
| | 45.9 | 0.090 | N.D | N.D | N.D | N.D |
| Total impurities 1 (including GSSG) | | 1.27 | 1.04 | 1.13 | 0.58 | 0.55 |
| Total impurities 2 (not including GSSG) | | 0.73 | 0.57 | 0.39 | 0.15 | 0.09 |

As shown in Table 3, it was found that as compared with the commercially available products A and B, and the crystal of reduced glutathione obtained in Comparative Example, in the crystals of the present invention, the content of L-cysteinyl-L-glycine is significantly low, and further, the contents of other impurities such as oxidized glutathione and γ-L-glutamyl-L-cysteinyl-L-alanine are also significantly low.

While the present invention has been described in detail with reference to specific embodiments, it is apparent to those skilled in the art that various changes and modifications can be made without departing from the spirit and scope of the present invention. The present application is based on Japanese Patent Application (Japanese Patent Application No. 2016-53844) filed on Mar. 17, 2016 and the entire contents of which are incorporated herein by reference. Further, all references cited herein are incorporated herein by reference in their entirety.

INDUSTRIAL APPLICABILITY

According to the present invention, a crystal of reduced glutathione having a reduced content of impurities, particularly L-cysteinyl-L-glycine and a method for producing the same are provided.

The invention claimed is:

1. An α-type crystal of reduced glutathione, wherein, in a high-performance liquid chromatography (HPLC) analysis, the peak area of L-cysteinyl-L-glycine is 0.02 or less with respect to the peak area of reduced glutathione which is taken as 100.

2. The α-type crystal of reduced glutathione according to claim 1, wherein in an HPLC analysis, the peak area of oxidized glutathione is 0.7 or less with respect to the peak area of reduced glutathione which is taken as 100.

3. The α-type crystal of reduced glutathione according to claim 2, wherein in an HPLC analysis, the total area of the other peaks is 1.0 or less with respect to the peak area of reduced glutathione which is taken as 100.

4. The α-type crystal of reduced glutathione according to claim 3, wherein in an HPLC analysis, the area of each of the other peaks excluding the peak of oxidized glutathione is 0.08 or less with respect to the peak area of reduced glutathione which is taken as 100.

5. The α-type crystal of reduced glutathione according to claim 2, wherein in an HPLC analysis, the area of each of the other peaks excluding the peak of oxidized glutathione is 0.08 or less with respect to the peak area of reduced glutathione which is taken as 100.

6. The α-type crystal of reduced glutathione according to claim 1, wherein in an HPLC analysis, the total area of the other peaks is 1.0 or less with respect to the peak area of reduced glutathione which is taken as 100.

7. The α-type crystal of reduced glutathione according to claim 6, wherein in an HPLC analysis, the area of each of the other peaks excluding the peak of oxidized glutathione is 0.08 or less with respect to the peak area of reduced glutathione which is taken as 100.

8. The α-type crystal of reduced glutathione according to claim 1, wherein in an HPLC analysis, the area of each of the other peaks excluding the peak of oxidized glutathione is 0.08 or less with respect to the peak area of reduced glutathione which is taken as 100.

9. A method for producing an α-type crystal of reduced glutathione in which in an HPLC analysis, the peak area of L-cysteinyl-L-glycine is 0.02 or less with respect to the peak area of reduced glutathione which is taken as 100, wherein the method comprising passing an aqueous solution containing reduced glutathione through a cation exchange resin with a high crosslinking degree, recovering the aqueous solution, precipitating an α-type crystal of reduced glutathione in the aqueous solution, and collecting the α-type crystal of reduced glutathione from the aqueous solution.

10. The production method according to claim 9, wherein the cation exchange resin with a high crosslinking degree is a cation exchange resin having a crosslinking degree of 12% or more.

11. The production method according to claim 10, wherein the cation exchange resin with a high crosslinking degree is a cation exchange resin having a sulfone group as a cation exchange group.

12. The production method according to claim 9, wherein the cation exchange resin with a high crosslinking degree is a cation exchange resin having a sulfone group as a cation exchange group.

* * * * *